(12) United States Patent
Srinivas et al.

(10) Patent No.: US 9,073,849 B2
(45) Date of Patent: Jul. 7, 2015

(54) PROCESS FOR MAKING DIMETHYL CARBONATE

(71) Applicant: COUNCIL OF SCIENTIFIC & INDUSTRIAL RESEARCH, New Delhi (IN)

(72) Inventors: Darbha Srinivas, Pune (IN); Unnikrishnan Pulikkeel, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/403,046

(22) PCT Filed: May 22, 2013

(86) PCT No.: PCT/IN2013/000331
§ 371 (c)(1),
(2) Date: Nov. 21, 2014

(87) PCT Pub. No.: WO2013/175510
PCT Pub. Date: Nov. 28, 2013

(65) Prior Publication Data
US 2015/0141690 A1    May 21, 2015

(30) Foreign Application Priority Data
May 22, 2012  (IN) .......................... 1559/DEL/2012

(51) Int. Cl.
*C07C 68/04* (2006.01)

(52) U.S. Cl.
CPC .................................... *C07C 68/04* (2013.01)

(58) Field of Classification Search
CPC ...................................................... C07C 68/04
See application file for complete search history.

(56) References Cited

PUBLICATIONS

Ikeda et al. "Promoting effect of phosphoric acid on zirconia catalysts in selective synthesis of dimethyl carbonate from methanol and carbon dioxide" Catalysis Letters, 2000, vol. 66, pp. 59-62.*
Wang et al. "Preparation of layered zirconium phosphonate/phosphate, zirconium phosphonate/phosphite and related compounds" Materials Chemistry and Physics, 1993, vol. 35, pp. 208-216.*
Clearfield, Abraham et al.; "Synthesis and Stability of Mixed Ligand Zirconium Phosphonate Layered Compounds"; Journal of Solid State Chemistry; vol. 117; No. 2; Jul. 1, 1995; pp. 275-289.
Ikeda, Yoshiki et al.; "Promoting effect of phosphoric acid on zirconia catalysts in selective synthesis of dimethyl carbonate from methanol and carbon dioxide"; Catalysis Letters; vol. 66; 2000; pp. 59-62.
Wang, J. Don et al.; "Preparation of layered zirconium phosphonate/phosphate, zirconium phosphonate/phosphite and related compounds"; Materials Chemistry and Physics; vol. 35; No. 3-4; Oct. 1, 1993; pp. 208-216.
International Preliminary Report on Patentability completed Jul. 30, 2014 for PCT/IN2013/000331, 7 pages.
International Search Report and Written Opinion mailed Aug. 5, 2013 for PCT/IN2013/000331, 11 pages.

* cited by examiner

*Primary Examiner* — Joseph Kosack
(74) *Attorney, Agent, or Firm* — Christie, Parker & Hale, LLP

(57) ABSTRACT

An eco-friendly process for making dimethyl carbonate comprising contacting methanol with carbon dioxide in the presence of a solid, calcined catalyst derived from zirconium phosphonate catalyst having molecular formula: $Zr(X)_{2-n} Y_n \cdot mH_2O$ where X refers to phosphonate, Y refers to $HPO_4^{2-}$ or $HPO_3^{2-}$, n varies from 0.2 to 1.8 and m varies from 0 to 5, is disclosed.

10 Claims, 4 Drawing Sheets

PROCESS FOR MAKING DIMETHYL CARBONATE

CROSS-REFERENCE TO RELATED APPLICATION

This application is a National Phase Patent Application and claims the priority of International Application Number PCT/IN2013/000331, filed on May 22, 2013, which claims priority of Indian Patent Application Number 1559/DEL/2012, filed on May 22, 2012. The disclosures of which are hereby incorporated by reference.

FIELD OF THE INVENTION

The present invention relates to a process for making dimethyl carbonate in presence of a solid catalyst.

Particularly, the present invention relates to an improved, eco-friendly process for producing dimethyl carbonate comprising contacting methanol with carbon dioxide in presence of a solid calcined catalyst derived from zirconium phosphonate having molecular formula:

$$Zr(X)_{2-n}Y_n \cdot mH_2O$$

wherein X refers to phosphonate and Y refers to $HPO_4^{2-}$ or $HPO_3^{2-}$. The value of n varies from 0.2 to 1.8 and the value of m varies from 0 to 5.

BACKGROUND OF THE INVENTION

Dimethyl carbonate, $(CH_3O)_2CO_3$ finds large industrial applications. It replaces toxic phosgene in the manufacture of polyurethanes and polycarbonates. It finds application as a "green" solvent and as an eco-friendly reagent in methylation, esterification, carbomethoxylation and carbonylation reactions. Dimethyl carbonate is also a potential oxygenate fuel additive replacement to MTBE. Three commercial methods of dimethyl carbonate production are known. Phosgenation of methanol is the route formerly used. Oxidative carbonylation of methanol in liquid or vapor phase using CuCl (U.S. Pat. No. 5,536,864), nitric oxide (UBE) or copper supported on active carbon (U.S. Pat. Nos. 5,183,920 and 5,543,548) catalysts is the second route. The third commercial method (also using $CO+O_2$) developed by UBE industry employs a $Pd^{2+}$ catalyst and an alkyl nitrite promoter. All these methods produce dimethyl carbonate in high yields but the chemicals used and vent discharges in the processes are toxic or corrosive.

Transesterification of cyclic carbonates with methanol is currently practiced at Asahi Corporation Ltd (U.S. Pat. No. 5,847,189A and 6,479,689B1). Dimethyl carbonate is produced in good yields. This reaction with small exotherm is carried out in the liquid phase without any toxic or corrosive chemicals. But alkelene diol in equimolar amounts is cogenerated. The one-pot reaction of epoxide, carbon dioxide and methanol produces dimethyl carbonate in moderate yields (U.S. Pat. Nos. 7,145,028; 6,607,279B1; 4,434,105 and 6,407,279 B1). Even in this reaction alkelene diol is cogenerated. Reaction of methanol with urea in presence of catalyst leads to dimethyl carbonate. Ammonia is produced as co-product which can be recycled back into urea production (U.S. Pat. Nos. 7,314,947 and 7,074,951). However, the reaction of dimethyl carbonate and ammonia leads to undesired carbamate and isocyanate products. All these processes of dimethyl carbonate synthesis are not atom-efficient. The co-products and their separation affect the economics of the process.

Direct synthesis of dimethyl carbonate by the reaction of methanol with carbon dioxide is the simplest and desirable route. Water is produced as a by-product in this reaction. This reaction is more atom-efficient than the above-said routes. However, yield of dimethyl carbonate is low in this reaction due to thermodynamic limitations. Development of more efficient catalysts that could activate simultaneously carbon dioxide and methanol and overcome the limitations is desirable. Moreover, utilizing carbon dioxide, a greenhouse emission gas, as a raw material in the production of a green chemical would possibly make some positive impact on reducing global warming and carbon dioxide levels in the atmosphere.

U.S. Pat. No. 7,605,285 B2 provides a method and apparatus for simultaneous production of methanol and dimethyl carbonate. Methanol is synthesized by allowing the synthesis gas to react over a catalyst, and dimethyl carbonate is produced by adding carbon dioxide to the methanol, characterized in that carbon dioxide in combustion exhaust gas discharged from a combustion radiator section for heating a reaction tube of the reformer is recovered. Dimethyl carbonate yields are limited by thermodynamic limitations.

US patent 2011/0196167 A1 discloses a method for producing dimethyl carbonate, the method comprises providing effective amounts of methanol and carbon dioxide to a reaction vessel, reacting methanol and carbon dioxide in the presence of a heterogeneous catalyst in the reaction vessel to produce dimethyl carbonate wherein the heterogeneous catalyst provides both acidic sites and basic sites. The catalyst is selected from the group consisting of $Rh/Al_2O_3$, $Pd/Al_2O_3$, $Pt/Al_2O_3$, $Ni/Al_2O_3$, $Rh/SiO_2$, $Rh/ZSM-5$, $Rh$—$K/Al_2O_3$, $Ni/SiO_2$—$Al_2O_3$, $Mo_2C/Al_2O_3$, $Pd/V_2O_5$, $Pd/TiO_2$, $Pd/V_2O_5$—$TiO_2$, $Pd/TiO_2$—$ZrO_2$, $Pt/Al_2O_3$, $Re/Al_2O_3$, $MoO_3/Al_2O_3$, $MoO_3/ZSM-5$, $MoO_3/SiO_2$ and combinations thereof. The reaction is performed at ambient temperature and at a temperature from about 80° C. to about 280° C. At 80° C., dimethyl carbonate is the selective product but at higher temperature, formation of significant amount of undesired dimethyl ether was detected.

References may be made to the following literature. Fang and Fujimoto (Appl. Catal. A: Gen. Vol. 142, Year 1996, Page L1) synthesized dimethyl carbonate from methanol and carbon dioxide using methyl iodide and $K_2CO_3$ as promoters. Although this reaction was fast, its deactivation was very rapid. Zirconia-based materials with both acidic and basic properties have been used as heterogenous catalysts for this reaction (Tomishige et al., J. Catal. Vol. 192, Year 2000, page 355; Ikeda et al., J. Phys. Chem. B Vol. 105, Year 2001, page 10653; Jiang et al., Appl. Catal. A: Gen., Vol. 256, Year 2003, page 203). The yield of DMC formed was low over these catalysts.

Article titled, "A novel method of direct synthesis of dimethyl carbonate from methanol and carbon dioxide catalyzed by zirconia" by Keiichi Tomishige, Tomohiro Sakaihori, Yoshiki Ikeda, Kaoru Fujimoto in Catalysis Letters, Year 1999, Volume 58, Issue 4, pp 225-229 reports the synthesis of Dimethyl carbonate from methanol and $CO_2$ with high selectivity using $ZrO_2$ catalysts. In this reaction, the amount of dimethyl ether and CO was below the detection limit. Further it reports, the catalytic activity seems to be related to acid-base-pair sites of the $ZrO_2$ surface from the results of temperature-programmed desorption of $NH_3$ and $CO_2$. It also reports the selectivity of DMC formation on Zirconia catalyst as 100% under all the reaction conditions studied.

Article titled, "Promoting effect of phosphoric acid on zirconia catalysts in selective synthesis of dimethyl carbonate from methanol and carbon dioxide" by Yoshiki Ikeda, Tomohiro Sakaihori, Keiichi Tomishige and Kaoru Fujimoto in Catalysis Letters 66 (2000) 59-62 reports the addition of phosphoric acid to zirconia catalysts promoted the activity for dimethyl carbonate synthesis from methanol and carbon dioxide with high selectivity, and the reactions proceeded at much lower temperature on $H_3PO_4/ZrO_2$ than on zirconia catalysts. It also suggests that the surface acidity enhancement by phosphoric acid contributed to higher activity. The selectivity of DMC formation on $H_3PO_4/ZrO_2$ is estimated 100%. The catalyst was optimized by employing calcinations temperature of 600° C. and P/Zr ratio of 0.05. However, even with this optimized catalyst the maximum yield of dimethyl carbonate produced at $CH_3OH:CO_2$ (milli molar ratio)=192:200, catalyst weight=0.5 g, reaction temperature=170° C. and reaction time=2 h was 0.85 mmol/g catalyst (0.0765 g. DMC/g. catalyst) only which is significantly low for possible commercialization.

In view of the importance of dimethyl carbonate in industrial applications and drawbacks of prior-art processes which include low yield of dimethyl carbonate, formation of undesired dimethyl ether and catalyst deactivation, it is desirable to have a more efficient solid catalyst and a process using the catalyst. The process of the present invention using zirconium phosphonate phosphite or zirconium phosphonate phosphate compound is highly efficient and overcomes the deficiencies of prior-art processes.

OBJECTIVES OF THE INVENTION

The prime object of present invention is to provide an efficient, eco-friendly process for making dimethyl carbonate in presence of a water-tolerant solid acid catalyst.

Another object of present invention is to provide a catalytic process for producing dimethyl carbonate wherein dimethyl carbonate is formed with 100% selectivity and catalyst is stable, reusable, active and selective over a broader range of temperatures and pressures.

Yet another object of the present invention is to provide a process wherein the solid catalyst is selectively gives dimethyl carbonate and no dimethyl ether.

SUMMARY OF THE INVENTION

Accordingly, present invention provides a process for making dimethyl carbonate in high yields and with 100 wt % selectivity wherein the said process comprises the steps of:
(a) providing reusable, water-tolerant, solid, calcined catalyst derived from zirconium phosphonate having molecular formula:

$Zr(X)_{2-n}Y_n.mH_2O$ 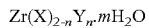

Wherein, X refers to phosphonate, Y refers to $HPO_4$ or $HPO_3^{2-}$, n varies from 0.2 to 1.8 and m varies from 0 to 5, prepared by the known method;
(b) contacting methanol with carbon dioxide in the presence of catalyst as provided in step (a) wherein the amount of catalyst ranges from 0.5 to 5% by weight of methanol, pressure of carbon dioxide ranges from 1 to 60 bar and molar ratio of methanol and carbon dioxide varies from 0.25:1 to 10:1;
(c) subjecting the reaction mixture as obtained in step (b) to a temperature in the range of 80 to 200° C. and for a period in the range of 3 to 12 hrs followed by lowering the temperature, venting out or recycling unreacted carbon dioxide and separating product dimethyl carbonate from the left out methanol, by-product water and catalyst by known procedures.

In an embodiment of the present invention, the reaction is carried out optionally in the presence of solvent or water trapping agent or both.

In another embodiment of the present invention, solvent used is selected from the group consisting of N,N-dimethyl formamide, tetrahydrofuran and dimethylsulphoxide.

The process according to claim 1, wherein water trapping agent used is selected from the group consisting of molecular sieves, 2,2-dimethoxy propane and like material.

In yet another embodiment of the present invention, said solid catalyst is hydrophobic with water adsorption capacity of 0.1-5 wt %.

In yet another embodiment of the present invention, said solid catalyst is stable and reusable and contains both acidic and basic sites.

In yet another embodiment of the present invention, said solid catalyst has the overall acid site density in the range of 0.05 to 0.35 mmol/sq. meter, basicity in the range of 0.05 to 0.5 mmol/g. catalyst and surface area in the range of 20-200 $m^2/g$.

In yet another embodiment of the present invention, carbon dioxide used in the reaction is 100% pure or a mixture of carbon dioxide and other gases wherein the other gases are carbon monoxide, hydrogen, hydrocarbons and water.

In yet another embodiment of the present invention, the composition of calcined solid catalyst comprises of zirconium pyrophosphate phase.

In yet another embodiment of the present invention, the yield of dimethyl carbonate is as high as or above 2.29 g/g. catalyst.

In still another embodiment of the present invention, the present invention provides a unique feature of the present invention wherein methanol is activated at both acidic and basic sites generating $CH_3^+$ and $CH_3O^-$ intermediate ions. Carbon dioxide is activated at the basic sites. Simultaneous presence both the acidic and basic sites and hydrophobicity of the catalyst are responsible for its efficient catalytic activity and reusability.

In yet another embodiment of the present invention, the reaction can be conducted in a batch, or continuous fixed-bed reaction mode.

In still yet another embodiment of the present invention, when the process is conducted in a continuous fixed-bed mode the catalyst is shaped into pellets or extrudates and used.

In yet another embodiment of the present invention, the selectivity of dimethyl carbonate is 100% by weight.

In still another embodiment, the present invention doesn't lead to production of dimethyl ether.

In yet another embodiment of the present invention, Zr in the catalyst composition can be replaced with other metal or metalloic ion preferably taken from the group consisting of Zr, Zn, Cd, Al, Sn, La and Ce.

In still yet another embodiment of the present invention, the catalyst of the present invention is characterized by powder X-ray diffraction pattern as shown in FIG. 1, infrared spectroscopic finger prints as shown in FIG. 2, $^{31}P$ magic angle spin nuclear magnetic resonance spectrum ($^{31}P$ MAS NMR) as shown in FIG. 3, the overall acid site density in the range 0.05 to 0.35 mmol/sq. meter, basicity in the range 0.05 to 0.5 mmol/g. catalyst and surface area in the range 20-200 $m^2/g$. In still another embodiment of the present invention, the process of present invention wherein the catalyst is a solid and the reaction takes place in a heterogeneous condition. The solid catalyst can be easily separated from products by centrifugation-filtration/decantation for further reuse. Also, the catalyst of present invention is stable in aqueous medium.

DETAILED DESCRIPTION OF THE INVENTION

Figure 1:
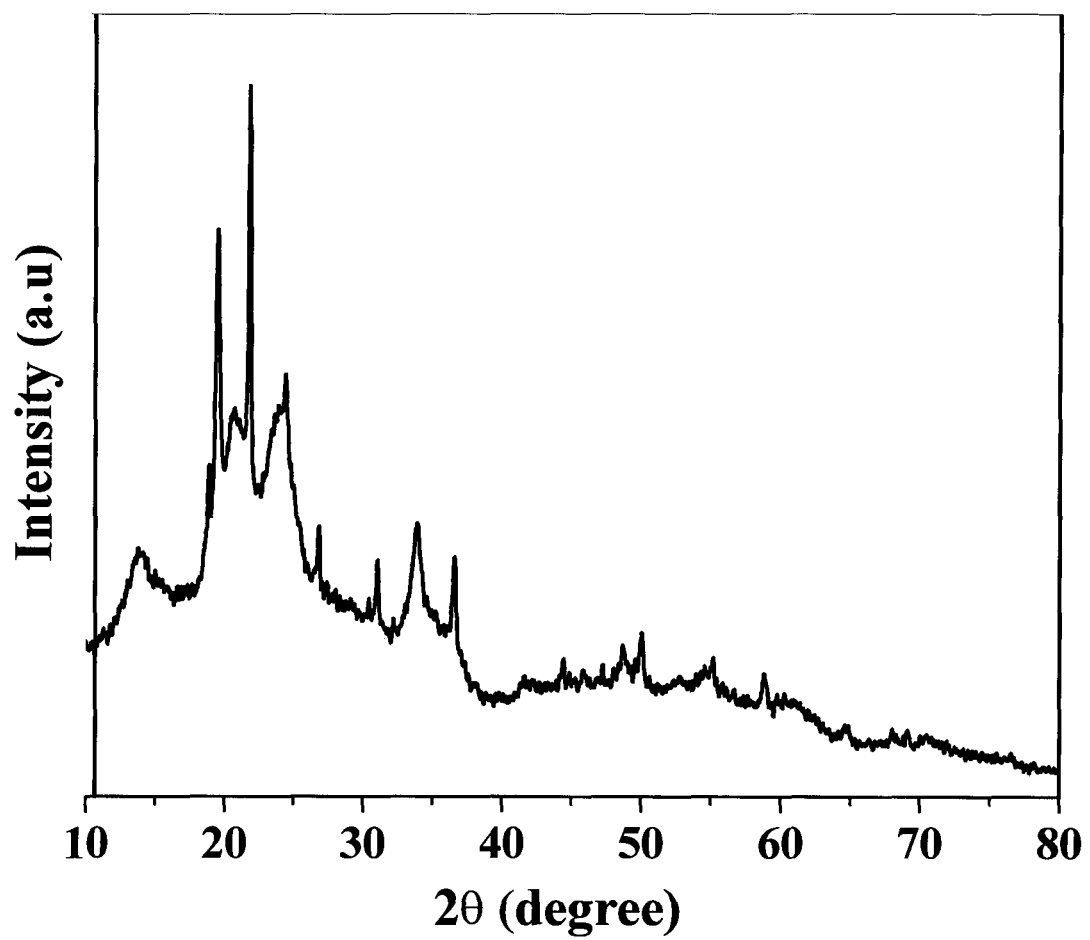
FIG. 1: X-ray diffraction pattern of the catalyst (Example 1).
Figure 2:
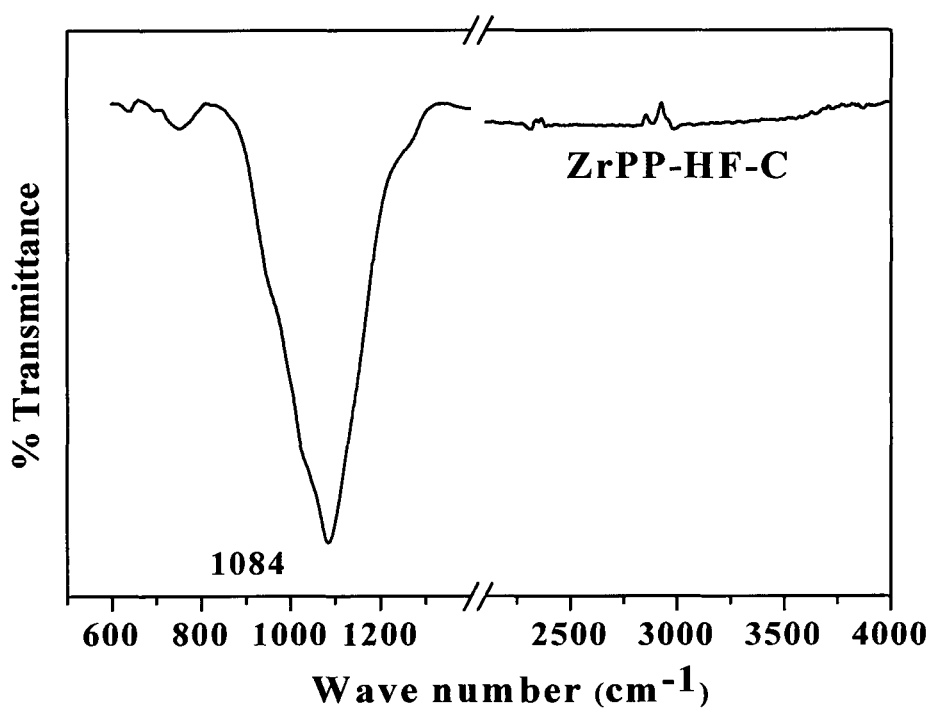
FIG. 2: FTIR spectrum of the catalyst.
Figure 3:
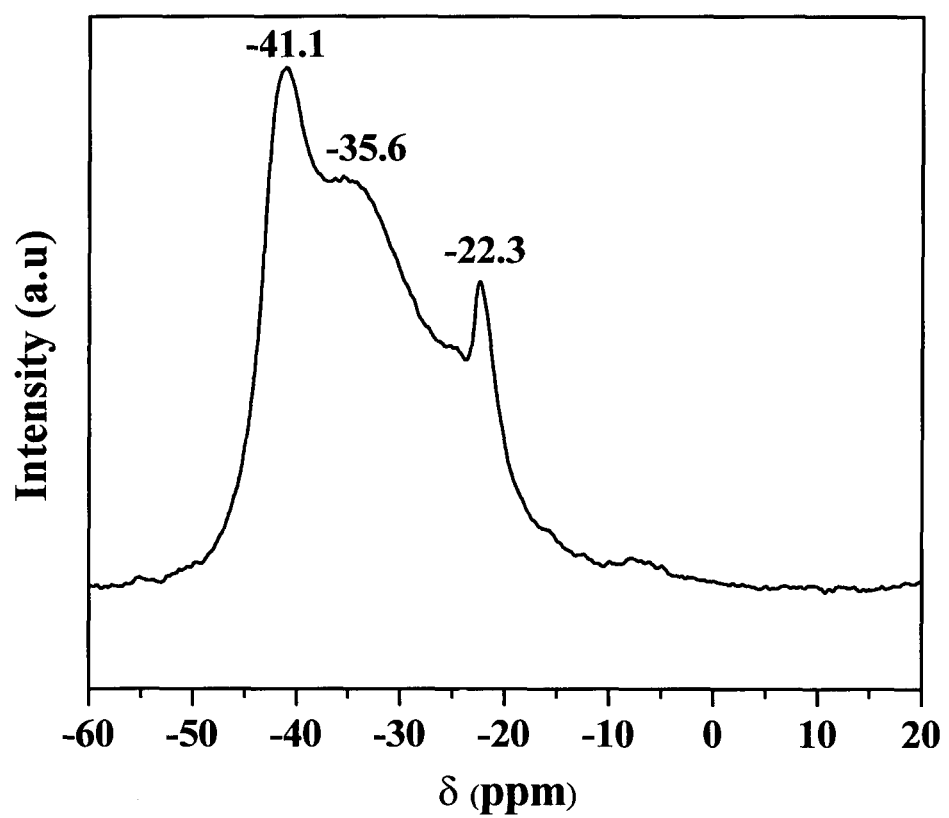
FIG. 3: $^{31}$P Magic angle spin nuclear magnetic resonance spectrum of catalyst.

The present invention discloses a process for making dimethyl carbonate in presence of a solid catalyst. The present invention discloses to an improved, eco-friendly process for producing dimethyl carbonate comprising contacting methanol with carbon dioxide in presence of a solid calcined catalyst derived from zirconium phosphonate having molecular formula:

$$Zr(X)_{2-n}Y_n.mH_2O$$

where X refers to phosphonate and Y refers to $HPO_4^{2-}$ or $HPO_3^{2-}$. The value of n varies from 0.2 to 1.8 and the value of m varies from 0 to 5.

In the investigations leading to the present invention, the solid, calcined zirconium phosphonate catalyst of present invention is highly efficient, high dimethyl carbonate yielding and could be easily separated from the products for further use. The prior-art catalysts are expensive due to presence of noble metals or less stable in water by-product medium. A highly stable and easily separable catalyst, for example, the catalyst of the present invention is advantageous.

The catalyst of the present invention is efficient in terms of the yield of dimethyl carbonate; 100% selectivity of dimethyl carbonate is obtained at a broader temperature and pressure range.

Present invention provides an improved process for making dimethyl carbonate in high yields with 100% selectivity wherein the said process comprises the steps of:
(a) contacting methanol with carbon dioxide in the presence of a reusable, water-tolerant, solid, calcined catalyst derived from zirconium phosphonate having molecular formula:

$$Zr(X)_{2-n}Y_n.mH_2O$$

where X refers to phosphonate and Y refers to $HPO_4^{2-}$ or $HPO_3^{2-}$. The value of n varies from 0.2 to 1.8 and the value of m varies from 0 to 5, wherein the amount of catalyst ranges from 0.5 to 5% by weight of methanol, pressure of carbon dioxide ranges from 1 to 60 bar and the molar ration of methanol to carbon dioxide ranges from 0.25:1 to 10:1;
(b) subjecting the reaction mixture obtained in step (a) to a temperature in the range of 80 to 200° C. and for a reaction time of 3 to 12 hrs to obtain dimethyl carbonate, and,
(c) lowering the temperature, venting out or recycling unreacted carbon dioxide and separating product dimethyl carbonate from the left out methanol, by-product water and catalyst by known procedures.

The process of present invention is eco-friendly, and generates little waste products unlike in the prior art processes where dimethyl ether formed in large quantities.

The zirconium phosphonate catalysts are prepared by the known procedure as described in the references: A. Clearfield et al., J. Sold. State Chem. Vol. 117, Year 1995, pp. 275; J. Don Wang et al., Mater. Chem. Phys. Vol. 35, Year 1993, pp. 208; K. Nakamura et al., J. Incl. Phenom. Mol. Recog. Chem. Vol. 31, Year 1998, pp. 351.

EXAMPLES

Following examples are given by way of illustration therefore should not be construed to limit the scope of the invention.

Example 1

This example illustrates the preparation of zirconium phenyl phosphonate phosphite catalyst of molecular composition: $Zr(C_6H_5PO_3)_{0.29}(HPO_3)_{1.71}.0.02H_2O$. In a typical synthesis, solution A was prepared by dissolving 4 g of zirconyl oxychloride ($ZrOCl_2.8H_2O$) in 40 ml of water and 9 ml of conc. HF taken in a polyethylene beaker. Solution B was prepared by dissolving 1.06 g of phenyl phosphonic acid and 26.8 g of phosphorous acid in 100 ml of water. Solution A was added to the solution B. Beaker containing solution A was rinsed with 14 ml of water and the contents were added to the reaction mixture. The reaction mixture was heated at 70° C. for 34 hrs till it got dried. The material was washed with 2 liters of water and dried at 90° C. for 16 h. The catalyst was calcined at 550° C. for 2 h. Acid site density=0.246 mmol/sq. meter, basicity=0.32 mmol/g, specific surface area=26 m$^2$/g and water adsorption capacity=0.2 wt %.

Example 2

This example illustrates the preparation of zirconium phenyl phosphonate phosphite catalyst of molecular composition: $Zr(C_6H_5PO_3)_{0.99}(HPO_3)_{1.01}.0.4H_2O$. In a typical synthesis, 1 g of phenyl phosphonic acid and 1.04 g of phosphorous acid were dissolved in 20 ml of water. To this, 2.04 g of zirconyl oxychloride dissolved in 5 ml of water was added. The mixture was then heated at 90° C. for 3 hrs and solid was recovered, washed with water and dried at 90° C. for 16 h. The catalyst was calcined at 550° C. for 2 h. Acid site density=0.051 mmol/sq. meter, basicity=0.15 mmol/g, specific surface area=188 m$^2$/g and water adsorption capacity=0.8 wt %.

Example 3

This example illustrates the preparation of zirconium phenyl phosphonate phosphite catalyst of molecular composition: $Zr(C_6H_5PO_3)_{0.97}(HPO_3)_{1.03}.0.15H_2O$. In a typical synthesis, 1 g of phenyl phosphonic acid and 0.52 g of phosphorous acid were dissolved in 20 ml of water. To this, 2.04 g of zirconyl oxychloride ($ZrOCl_2.8H_2O$) dissolved in 5 ml of water was added. The mixture was then heated at 90° C. for 3 hrs and solid was recovered, washed with water and dried at 90° C. for 16 h. The catalyst was calcined at 550° C. for 2 h. Acid site density=0.05 mmol/sq. meter, basicity=0.17 mmol/g, specific surface area=193 m$^2$/g and water adsorption capacity=2.1 wt %.

Example 4

This example illustrates the preparation of zirconium phenyl phosphonate phosphate catalyst of molecular composition: $Zr(C_6H_5PO_3)_{0.8}(HPO_4)_{1.2}.0.5H_2O$. In a typical synthesis, solution A was prepared by dissolving 5.43 g of zirconyl oxychloride in 30 ml of distilled water taken in a polyethylene beaker. To it 12.4 ml of 48% HF was added. Solution B was prepared by disallowing 2.16 g of phenyl phosphonic acid in 45 ml of water. To it 84.6 ml of conc. phosphoric acid was added. Solution A was added slowly at 25° C. to solution B over a period of 1 h. The empty beaker containing solution A was rinsed with 28 ml of water and the contents were added to the above reaction mixture. The combined volume of the reaction mixture was nearly 200 ml. The mixture was heated in oil bath at 70° C. for 2 days till all the solvent got evaporated and solid was formed. The solid was washed with 2 l of water, dried in an oven at 90° C. for 16 h. The material was calcined at 550° C. for 2 h. Acid site density=0.09 mmol/sq. meter, basicity=0.20 mmol/g, specific surface area=200 $m^2/g$ and water adsorption capacity=0.7 wt %.

Example 5

This example illustrates the preparation of dimethyl carbonate using the calcined catalyst described in Example 1. 5.2 g of methanol (164 mmol), 0.102 g of catalyst, 10 ml of N,N-dimethyl formamide (solvent) and 0.5 g of molecular sieves-3A were taken in a 100 ml stainless steel Parr autoclave. The reactor was pressurized with carbon dioxide (98 vol %; rest being CO, $CH_4$, hydrogen and $H_2O$) to 40 bar (164 mmol). Temperature of the reactor was raised to 170° C. and the reaction was conducted for 12 h. Later, unreacted gases were vented out. The catalyst was separated from the liquid product by filtration. The liquid product was analyzed by gas chromatography (Varian 3400). Nonane-1-ol was used an internal standard. Dimethyl carbonate yield=2.29 g/g catalyst. Gas portion did not contain any detectable dimethyl ether or carbon monoxide compound. Mass balance >95 wt %.

Example 6

This example illustrates the preparation of dimethyl carbonate using the calcined catalyst described in Example 1. 5.2 g of methanol (164 mmol), 0.160 g of catalyst, 10 ml of N,N-dimethyl formamide (solvent) and 0.5 g of molecular sieves-3A were taken in a 100 ml stainless steel Parr autoclave. The reactor was pressurized with carbon dioxide (98 vol %; rest being CO, $CH_4$, hydrogen and $H_2O$) to 40 bar (164 mmol). Temperature of the reactor was raised to 170° C. and the reaction was conducted for 12 h. Later, unreacted gases were vented out. The catalyst was separated from the liquid product by filtration. The liquid product was analyzed by gas chromatography (Varian 3400). Nonane-1-ol was used an internal standard. Dimethyl carbonate yield=1.62 g/g catalyst. Gas portion did not contain any detectable dimethyl ether or carbon monoxide compound. Mass balance >95 wt %.

Example 7

This example illustrates the preparation of dimethyl carbonate using the calcined catalyst described in Example 1 at $CO_2$ pressure of 30 bar and methanol:$CO_2$ molar ratio of 2:1. 8 g of methanol (250 mmol), 0.1602 g of catalyst, 10 ml of N,N-dimethyl formamide (solvent) and 0.5 g of molecular sieves-3A were taken in a 100 ml stainless steel Parr autoclave. The reactor was pressurized with carbon dioxide (98 vol %; rest being CO, $CH_4$, hydrogen and $H_2O$) to 30 bar (125 mmol). Temperature of the reactor was raised to 170° C. and the reaction was conducted for 12 h. Later, unreacted gases were vented out. The catalyst and molecular sieve were separated from the liquid product by filtration. The liquid product was analyzed by gas chromatography (Varian 3400). Nonane-1-ol was used an internal standard. Dimethyl carbonate yield=1.12 g/g catalyst. Mass balance >95 wt %.

Example 8

This example illustrates the preparation of dimethyl carbonate using the calcined catalyst described in Example 1 at $CO_2$ pressure of 30 bar, methanol:$CO_2$ molar ratio of 4:1 and without employing a water trapping agent. 16.02 g of methanol (500 mmol), 0.1602 g of catalyst and 10 ml of N,N-dimethyl formamide (solvent) were taken in a 100 ml stainless steel Parr autoclave. The reactor was pressurized with carbon dioxide (98 vol %; rest being CO, $CH_4$, hydrogen and $H_2O$) to 30 bar. Temperature of the reactor was raised to 170° C. and the reaction was conducted for 12 h. Later, unreacted gases were vented out. The catalyst was separated from the liquid product by filtration. The liquid product was analyzed by gas chromatography (Varian 3400). Nonane-1-ol was used an internal standard. Dimethyl carbonate yield=0.84 g/g catalyst. Mass balance >95 wt %.

Example 9

This example illustrates the preparation of dimethyl carbonate using the calcined catalyst described in Example 1 at $CO_2$ pressure of 30 bar, methanol:$CO_2$ molar ratio of 4:1 and without employing solvent and water trapping agent. 16.02 g of methanol (500 mmol), and 0.1602 g of catalyst were taken in a 100 ml stainless steel Parr autoclave. The reactor was pressurized with carbon dioxide (98 vol %; rest being CO, $CH_4$, hydrogen and $H_2O$) to 30 bar. Temperature of the reactor was raised to 170° C. and the reaction was conducted for 12 h. Later, unreacted gases were vented out. The catalyst was separated from the liquid product by filtration. The liquid product was analyzed by gas chromatography (Varian 3400). Nonane-1-ol was used an internal standard. Dimethyl carbonate yield=0.72 g/g catalyst. Mass balance >95 wt %.

Example 10

This example illustrates the preparation of dimethyl carbonate using the calcined catalyst described in Example 1 at $CO_2$ pressure of 30 bar, methanol:$CO_2$ molar ratio of 4:1, without employing solvent but using a water trapping agent—molecular sieve. 16.02 g of methanol (500 mmol), 0.1602 g of catalyst and 0.5 g of molecular sieve-3A were taken in a 100 ml stainless steel Parr autoclave. The reactor was pressurized with carbon dioxide (98 vol %; rest being CO, $CH_4$, hydrogen and $H_2O$) to 30 bar. Temperature of the reactor was raised to 170° C. and the reaction was conducted for 12 h. Later, unreacted gases were vented out. The catalyst and molecular sieve were separated from the liquid product by filtration. The liquid product was analyzed by gas chromatography (Varian 3400). Nonane-1-ol was used an internal standard. Dimethyl carbonate yield=0.91 g/g catalyst. Mass balance >95 wt %.

Example 11

This example illustrates the preparation of dimethyl carbonate using the calcined catalyst described in Example 1 at 20 bar $CO_2$ pressure, 1 wt % of catalyst and without employing solvent and water trapping agent. 16.02 g of methanol (500 mmol) and 0.160 g of catalyst were taken in a 100 ml stainless steel Parr autoclave. The reactor was pressurized with carbon dioxide (98 vol %; rest being CO, $CH_4$, hydrogen and $H_2O$) to 20 bar (83 mmol). Temperature of the reactor was raised to 170° C. and the reaction was conducted for 8 h.

Figure 4:
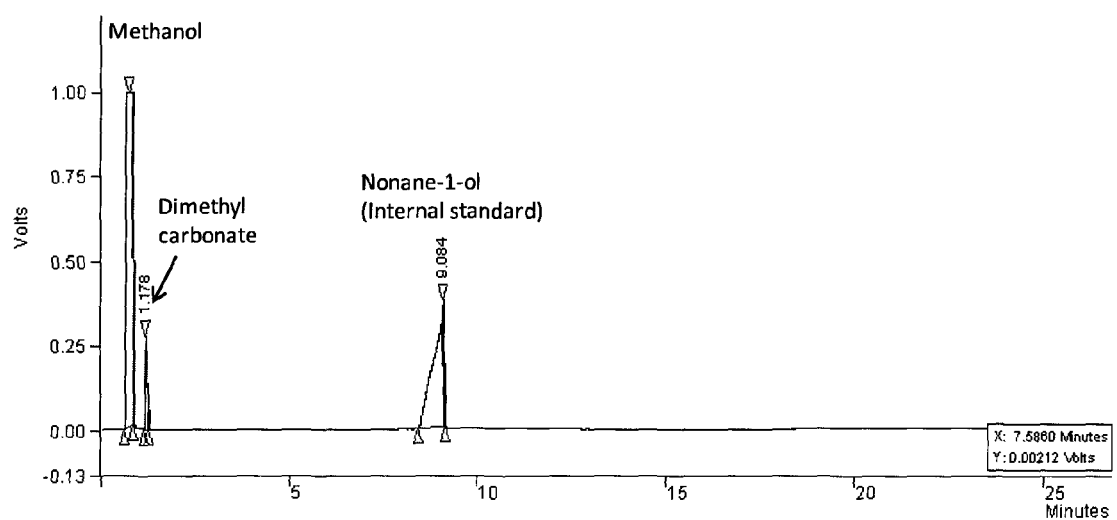
FIG. 4: Gas chromatograph of the product mixture (Example 10)

Later, unreacted gases were vented out. The catalyst was separated from the liquid product by filtration. The liquid product was analyzed by gas chromatography (Varian 3400). Nonane-1-ol was used an internal standard. Dimethyl carbonate yield=0.46 g/g catalyst. Mass balance=99 wt %. FIG. 4 shows the gas chromatograph of the product mixture.

Example 12

This example illustrates the preparation of dimethyl carbonate using the calcined catalyst described in Example 2 at 20 bar $CO_2$ pressure, 1 wt % of catalyst and without employing solvent and water trapping agent. 16.02 g of methanol (500 mmol) and 0.160 g of catalyst were taken in a 100 ml stainless steel Parr autoclave. The reactor was pressurized with carbon dioxide to 20 bar (83 mmol). Temperature of the reactor was raised to 170° C. and the reaction was conducted for 8 h. Later, unreacted gases were vented out. The catalyst was separated from the liquid product by filtration. The liquid product was analyzed by gas chromatography (Varian 3400). Nonane-1-ol was used an internal standard. Dimethyl carbonate yield=0.045 g/g catalyst. Mass balance=99 wt %.

Example 13

This example illustrates the preparation of dimethyl carbonate using the calcined catalyst described in Example 3 at 20 bar $CO_2$ pressure, 1 wt % of catalyst and without employing solvent and water trapping agent. 16.02 g of methanol (500 mmol) and 0.160 g of catalyst were taken in a 100 ml stainless steel Parr autoclave. The reactor was pressurized with carbon dioxide to 20 bar (83 mmol). Temperature of the reactor was raised to 170° C. and the reaction was conducted for 8 h. Later, unreacted gases were vented out. The catalyst was separated from the liquid product by filtration. The liquid product was analyzed by gas chromatography (Varian 3400). Nonane-1-ol was used an internal standard. Dimethyl carbonate yield=0.05 g/g catalyst. Mass balance=99 wt %. FIG. 4 shows the gas chromatograph of the product mixture.

Example 14

This example illustrates the preparation of dimethyl carbonate using the calcined catalyst described in Example 4 at 20 bar $CO_2$ pressure, 1 wt % of catalyst and without employing solvent and water trapping agent. 16.02 g of methanol (500 mmol) and 0.160 g of catalyst were taken in a 100 ml stainless steel Parr autoclave. The reactor was pressurized with carbon dioxide to 20 bar (83 mmol). Temperature of the reactor was raised to 170° C. and the reaction was conducted for 8 h. Later, unreacted gases were vented out. The catalyst was separated from the liquid product by filtration. The liquid product was analyzed by gas chromatography (Varian 3400). Nonane-1-ol was used an internal standard. Dimethyl carbonate yield=0.16 g/g catalyst. Mass balance=99 wt %.

Example 15

This example illustrates the reusability of the catalyst reported in example 1 in four recycling experiments. In this study 16.02 g of methanol (500 mmol), 0.1602 g of catalyst and 5 ml of N,N-dimethyl formamide (solvent) were taken in a 100 ml stainless steel Parr autoclave. The reactor was pressurized with carbon dioxide to 30 bar (125 mmol). Temperature of the reactor was raised to 170° C. and the reaction was conducted for 12 h. Later, unreacted gases were vented out. The catalyst was separated from the liquid product by filtration. The liquid product was analyzed by gas chromatography (Varian 3400). Nonane-1-ol was used an internal standard. The catalyst recovered after washing with acetone (5 ml) and drying at 250° C. for 2 h was used in the recycling experiment conducted in the same manner as described above. Such recycling studies of the catalyst were done four times.

Dimethyl carbonate yield=0.805 g/g catalyst (Fresh or $0^{th}$ recycle), 0.805 g/g catalyst ($1^{st}$ recycle), 0.803 g/g catalyst ($2^{nd}$ recycle), 0.804 g/g catalyst ($3^{rd}$ recycle) and 0.788 g/g catalyst ($4^{th}$ recycle).

Example 16

This example compares the performance of calcined $H_3PO_4/ZrO_2$ catalyst prepared as reported in the prior art by Yoshiki Ikeda, Tomohiro Sakaihori, Keiichi Tomishige and Kaoru Fujimoto (Catalysis Letters, Vol. 66, Year 2000, pp. 59-62) with that of the catalyst of present invention reported in Example 1. The comparative experiments were conducted under similar experimental conditions as reported in Example 6. 5.2 g of methanol (164 mmol), 0.160 g of calcined $H_3PO_4/ZrO_2$ catalyst, 10 ml of N,N-dimethyl formamide (solvent) and 0.5 g of molecular sieves-3A were taken in a 100 ml stainless steel Parr autoclave. The reactor was pressurized with carbon dioxide (98 vol %; rest being CO, $CH_4$, hydrogen and $H_2O$) to 40 bar (164 mmol). Temperature of the reactor was raised to 170° C. and the reaction was conducted for 12 h. Later, unreacted gases were vented out. The catalyst was separated from the liquid product by filtration. The liquid product was analyzed by gas chromatography (Varian 3400). Nonane-1-ol was used as internal standard. DMC yield=0.17 g/g catalyst. Gas portion did not contain any detectable dimethyl ether or carbon monoxide compound. Mass balance >95 wt %. Under similar conditions the calcined catalyst of Example 1 provided Dimethyl carbonate yield of 1.62 g/g catalyst. Hence, the catalyst of present invention is nearly 10 times more active and efficient than the prior art catalyst.

ADVANTAGES OF THE INVENTION

Advantages of instant invention are as following:
1. Heterogeneous, bi-functional, hydrophobic catalyst-based process
2. Reusable catalyst process
3. Eco-friendly process
4. Dimethyl carbonate selectivity of 100% by weight.
5. Reaction can be performed either in batch or continuous fixed-bed reaction mode.

The invention claimed is:
1. A process for making dimethyl carbonate in yield a greater than 40 wt % of catalyst and with 100 wt % selectivity wherein the process comprises the steps of:
(a) providing reusable, water-tolerant, solid, calcined catalyst consisting of zirconium pyrophosphate derived from zirconium phosphonate having a molecular formula:

$Zr(X)_{2-n}Y_n \cdot mH_2O$ wherein, X refers to phenyl phosphonate, Y refers to $HPO_4^{2-}$ or $HPO_3^{2-}$, n varies from 0.2 to 1.8 and m varies from 0 to 5;
(b) contacting methanol with carbon dioxide in the presence of the catalyst as provided in step (a) wherein the amount of the catalyst ranges from 0.5 to 5% by weight of methanol, pressure of carbon dioxide ranges from 1 to 60 bar and a molar ratio of methanol and carbon dioxide varies from 0.25:1 to 10:1; and (c) subjecting the reaction mixture as obtained in step (b) to a temperature in the range of 80 to 200° C. and for a period in the range of 3 to 12 hrs followed by lowering the temperature, venting out or recycling unreacted carbon dioxide and separating product dimethyl carbonate from the left out methanol, by-product water and catalyst.

2. The process according to claim 1, wherein the reaction is carried out in the presence of a solvent selected from the group of N,N-dimethyl formamide, tetrahydrofuran and dimethylsulphoxide.

3. The process according to claim 1, wherein the reaction is carried out in the presence of a water trapping agent selected from the group of molecular sieves, 2,2-dimethoxy propane and like material.

4. The process according to claim 1, wherein the reaction is carried out in presence of either or both the solvent and the water trapping agent.

5. The process according to claim 1, wherein the catalyst is hydrophobic with water absorption capacity in the range of 0.1-5 wt %.

6. The process according to claim 1, wherein the catalyst contains both acidic and basic sites.

7. The process according to claim 1, wherein the overall acid site density of the catalyst is in the range of 0.02 to 0.35 mmol/sq. meter, basicity is in the range of 0.05 to 0.5 mmol/g.catalyst and surface area is in the range of 20-200 $m^2/g$.

8. The process according to claim 1, wherein carbon dioxide used in the reaction is 100% pure or a mixture of carbon dioxide and other gases wherein the other gases are carbon monoxide, hydrogen, hydrocarbons and water.

9. The process according to claim 1, wherein the catalyst is stable.

10. The process according to claim 1, wherein a yield of dimethyl carbonate is ≥2.29 g/g. catalyst or 229 wt % of catalyst.

* * * * *